United States Patent [19]

Alexander, Jr. et al.

[11] Patent Number: 5,735,791
[45] Date of Patent: Apr. 7, 1998

[54] INFLATABLE HEART ELEVATION APPARATUS AND METHOD

[75] Inventors: John C. Alexander, Jr., Kenilworth, Ill.; Carl A. Swindle, Salt Lake City, Utah

[73] Assignee: Research Medical, Inc., West Midvale, Utah

[21] Appl. No.: 856,255

[22] Filed: May 14, 1997

Related U.S. Application Data

[60] Provisional application No. 60/037,011, Jan. 31, 1997.
[51] Int. Cl.$^6$ ............................................. A61B 17/00
[52] U.S. Cl. ............................................. 600/37; 600/207
[58] Field of Search ............................ 600/37, 201, 206, 600/207, 208, 235; 601/151, 152, 153; 606/191, 192

[56] References Cited

U.S. PATENT DOCUMENTS

| | | | |
|---|---|---|---|
| 4,637,377 | 1/1987 | Loop | 600/37 |
| 4,947,843 | 8/1990 | Wright et al. | |
| 5,400,773 | 3/1995 | Zhu et al. | 600/207 |
| 5,453,078 | 9/1995 | Valentine et al. | 600/37 |

*Primary Examiner*—Jeffrey A. Smith
*Attorney, Agent, or Firm*—Workman, Nydegger & Seeley

[57] ABSTRACT

The present invention is directed to new and useful methods and apparatus for improving access to the heart during cardiac surgery, while avoiding damage to the phrenic nerves. The present invention comprises a heart elevation apparatus which is soft and substantially cylindrical, with substantially flat anterior and posterior surfaces. Upon inflation, the anterior surface stabilizes the positioning of the heart and prevents the heart from falling off of the apparatus. The flat posterior surface facilitates positioning of the apparatus on the chest wall. An insulation pad on the posterior surface serves to insulate the phrenic nerves from the frigid bathes commonly employed in cardiac surgical procedures, and also protects the nerves from any compressive forces exerted during the surgery. A web member in the interior of the inflatable chamber prevents the inflatable chamber from blowing up into a ball, and instead constrains the anterior and posterior surfaces, thus resulting in flat or concave appearance, depending on the level of inflation in the inflation chamber. Insertion and proper placement of the apparatus in a deflated state is preferably through an incision in the thoracic wall or through an opening in the sternum. The apparatus is positioned beneath the heart along the chest wall, such that the heart balances stably thereon. The apparatus is then selectively inflated, which elevates the heart and improves the surgeons access thereto. After completion of the cardiac surgical procedure, the apparatus is deflated and then removed from the patient.

20 Claims, 3 Drawing Sheets

INFLATABLE HEART ELEVATION APPARATUS AND METHOD

BACKGROUND OF THE INVENTION

1. Related Application

Benefit of the earlier filing date of Provisional Patent Application Ser. No. 60/037,011, filed Jan. 31, 1997, is claimed for this application under Section 119(e) of Title 35 of the United States Code.

2. The Field of the Invention

The present invention is directed generally to methods and apparatus for accessing a surgical site during a surgical procedure. More specifically, the present invention is directed to methods and apparatus for accessing the heart during cardiac surgical procedures.

3. The Relevant Technology

Surgical procedures inherently require access to the diseased or damaged tissue necessitating the surgery. During cardiac surgical procedures for example, it is necessary to obtain access to the heart appropriate to the surgery to be performed. However, the heart is well protected beneath the sternum, the rib cage, and many layers of connective tissue. Thus, in many cardiac procedures, a surgeon performs a medium sternotomy wherein the sternum is split and the multiple tissue layers are dissected away in order to obtain sufficient access to the heart. The heart may be housed in such a cavernous chest cavity that the surgeon works literally up to his elbows inside the patient.

Alternatively, a surgeon may perform a thoracotomy wherein an incision is made between two ribs, or portions of the rib cage are removed, to obtain access to the heart. Yet the resulting surgical field is constrained by the size of the opening and the distance of the heart therefrom.

Furthermore, during cardiac surgical procedures it is common for the surgical team to significantly cool the cardiac tissue by introducing cold, sterile saline into the chest cavity. However, this may damage the phrenic nerves which run through the chest cavity, posterior to the heart. In turn, cardiac patients may leave the procedure with additional injuries, and pain or even paralysis in the tissues innervated by the phrenic nerves.

Conventionally surgeons have stacked gauze pads underneath the heart in an attempt to facilitate access thereto. Such a system offers the surgeon little selective control over the pads once inserted. Furthermore, the pads are not fluid-resistant, and absorb fluid, such as the cold saline, in the chest cavity. The soaked pads may put pressure on the phrenic nerves, and offer no insulation from the cold saline. The use of gauze is a burdensome make-shift system at best.

SUMMARY AND OBJECTS OF THE INVENTION

It is therefore a primary object of the present invention to provide effective methods and apparatus for improving access to the heart during cardiac surgical procedures, and improving presentation of the heart to the surgical field.

Still another object of the present invention is to provide methods and apparatus for elevating the heart in the chest cavity.

Another object of the present invention is to provide methods and apparatus for maintaining a level and stable cardiac surgical field.

Yet another object of the present invention is to provide methods and apparatus which facilitate ease of insertion, positioning, inflation, deflation, and removal thereof.

It is another object of the present invention to provide methods and apparatus for protecting and insulating the phrenic nerves during cardiac surgical procedures.

To achieve the foregoing objects, and in accordance with the invention as embodied and broadly described herein, the present invention is directed to new and useful methods and apparatus for presenting the heart for better access in cardiac surgery, while avoiding damage to the phrenic nerves. The present invention preferably comprises an inflatable heart elevation apparatus including an inflatable chamber, inflation tubing, a valve, and an insulation pad. The inflatable chamber is soft and substantially cylindrical, with rounded edges and substantially flat anterior and posterior surfaces. The flat anterior surface stabilizes the positioning of the heart on the inflatable chamber, and prevents the heart from tipping or falling off. The flat posterior surface facilitates positioning of the inflatable chamber on the chest wall or pericardial cavity.

In addition, attached to the flat posterior surface is an insulation pad, which serves to insulate the phrenic nerves from the frigid bathes commonly employed in cardiac surgical procedures and also protects the nerves from any compressive forces exerted by the weight of present invention in concert with the weight of the heart and the surgery being performed thereon.

Furthermore, it is a feature of the present invention that a web member in the interior of the inflatable chamber prevents the inflatable chamber from blowing up into a ball. Instead the web member constrains the anterior and posterior surfaces, thus resulting in a flat or concave appearance, depending on the level of inflation in inflation chamber. Upon inflation through valve and inflation tubing, the inflatable chamber is sized to accommodate the bulk of the heart muscle. In addition, upon inflation, the inflatable chamber provides approximately 0 to 6 centimeters of lift from the chest wall in an embodiment preferred for an adult human.

To use the system of the present invention, the first step preferably includes insertion and proper placement of the apparatus in a deflated state through an incision in the thoracic wall or through an opening in the sternum. The apparatus is then positioned beneath the heart along the chest wall, such that the heart balances stably thereon. The apparatus is then selectively inflated, which elevates the heart and improves the surgeon's access thereto. After completion of the cardiac surgical procedure, the apparatus is deflated by applying suction in the form a syringe or a vacuum, and then the apparatus is removed from the patient.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

During surgery, it is often necessary to cut through protective bone, muscle, and connective tissue layers to access the requisite anatomy. In cardiac surgical procedures, for example, surgeons typically cut through either the sternum or the rib cage to access the heart. Yet, the posterior position of the heart in the chest cavity, especially when the patient is lying down, impedes a surgeon's access to the heart. In large patients, a surgeon may be required to insert a significant portion of his or her arm into the chest cavity to reach the heart. In turn, the surgeon's visual field may be obstructed, and the surgical process may be impeded. It would therefore be a substantial benefit to ameliorate access to the heart during such procedures, for both surgeons and patients.

In addition, surgeons have conventionally cooled the heart during many cardiac procedures in order to slow the heart's uptake of oxygen and give the surgeon a greater window of time in which to complete the surgery. In order to cool the heart, surgeons often bathe the chest cavity with cold, sterile saline. However, this frigid bath occasionally results in shock to the phrenic nerves, the nerves that run through the chest cavity posterior to the heart. In turn, the tissues innervated by the phrenic nerves may develop temporary or possibly permanent paralysis. For cardiac patients, it would therefore be a substantial benefit to protect the phrenic nerve from such frigid shock during cardiac surgical procedures.

Figure 1:
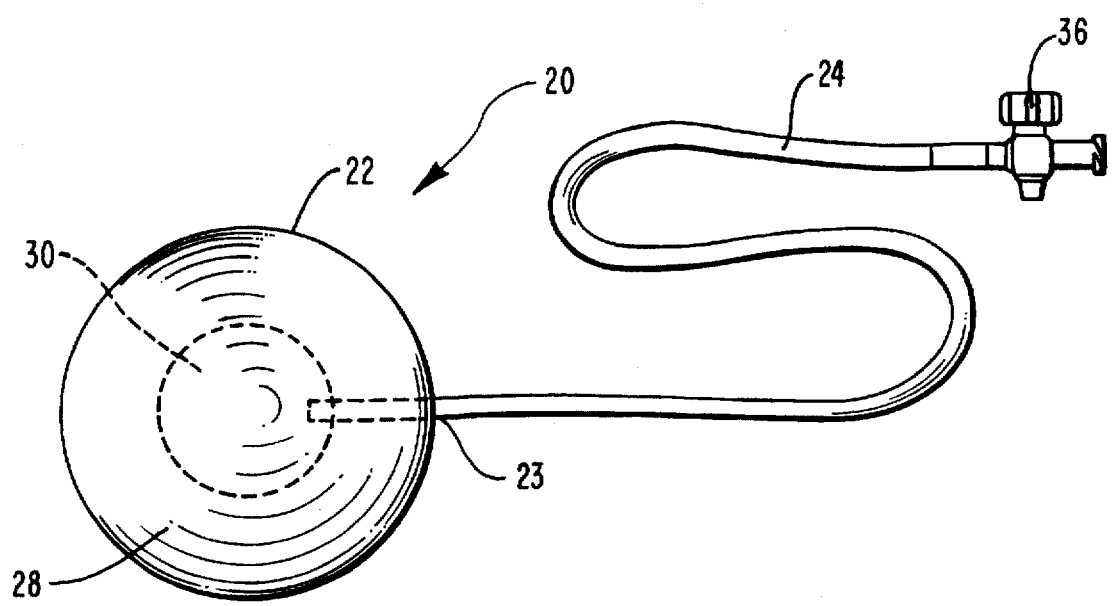
FIG. 1 is a top view of a preferred embodiment of the apparatus of the present invention.
Figure 2:
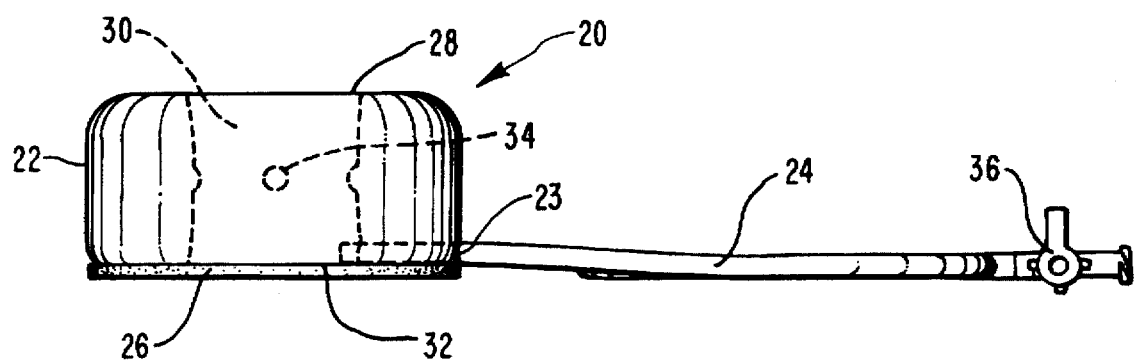
FIG. 2 is a side view of the embodiment of FIG. 1.

FIGS. 1 and 2 illustrate features of the present invention that solve the problems illustrated above with respect to cardiac surgical procedures. In particular, the present invention relates to methods and apparatus for improved access to the heart during cardiac surgical procedures, while avoiding damage to the phrenic nerves.

As illustrated in FIG. 1, the present invention comprises an inflatable heart elevation apparatus, represented generally by number 20. The heart elevation apparatus includes an inflatable chamber 22 to which is attached an inflation tubing 24.

Inflatable chamber 22 preferably comprises a urethane composition. The soft durometer of a urethane composition helps prevent damage to the delicate cardiac tissue and chest wall. It should be understood, however, that other soft materials would be within the scope of the present invention. For example, inflatable chamber 22 could alternatively comprise silicone, polyvinyl chloride, or other materials having a durometer of about 20 shore A to about 90 shore D.

Inflatable chamber 22 is preferably substantially cylindrical, as illustrated in FIGS. 1 and 2. With rounded edges and no sharp corners, such a shape helps prevent damage to the surrounding tissue. It will be appreciated in view of the teachings herein, however, that other shapes could also be used in order to obtain the benefits of the present invention.

Figure 3:
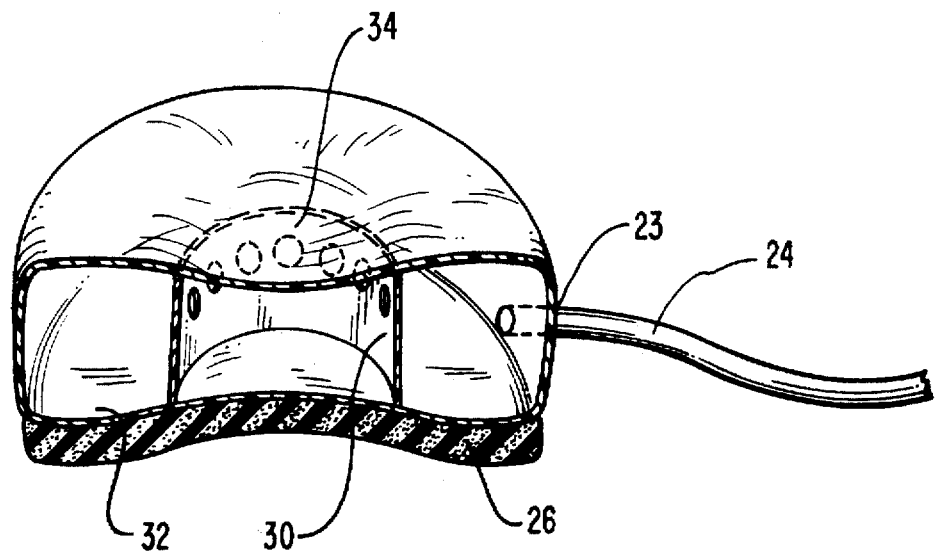
FIG. 3 is a cross sectional view of an alternate embodiment of the apparatus of the present invention.
Figure 4:
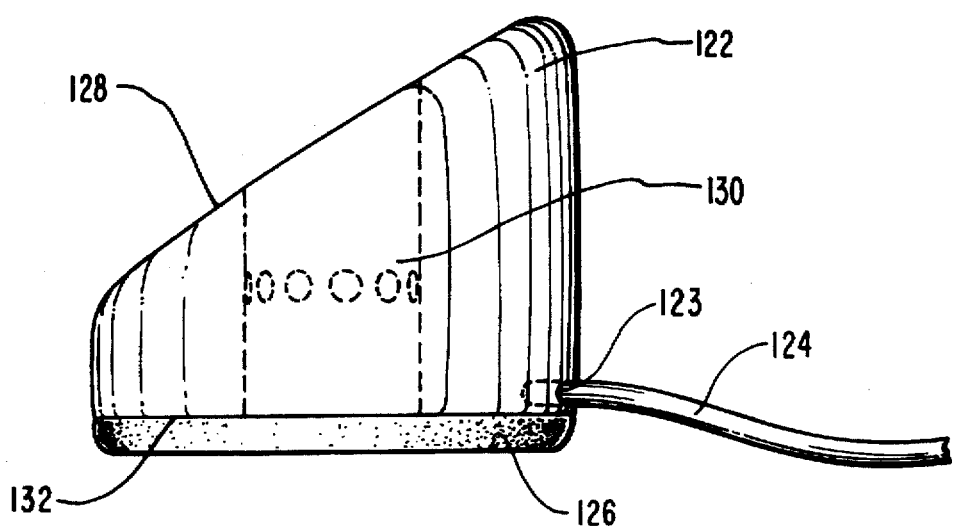
FIG. 4 is a side view of yet another alternate embodiment of the apparatus of the present invention.

It is a feature of the present invention that inflatable chamber 22 comprises substantially flat anterior and posterior surfaces. The flat anterior surface 28 offers a level base on which the heart will sit for most cardiac surgical procedures. Such a level surface stabilizes the positioning of the heart on the inflatable chamber, and prevents the heart from tipping or falling off. For some cardiac procedures the anterior surface may comprise a concave appearance as illustrated in FIG. 3, or a tapered appearance as illustrated in FIG. 4.

The shape and positioning of the anterior surface is advantageously accomplished via construction of a web member 30 in the interior of inflatable chamber which prevents the inflatable chamber from blowing up into a ball. Instead web member 30 constrains the anterior surface, thus resulting in a generally flat appearance as illustrated in FIG. 2, or a generally concave appearance as illustrated in FIG. 3. Alternatively, as illustrated in FIG. 4, the web member 130 and inflation chamber 122 may be tapered to produce a tapered anterior surface 128. It will be appreciated that other shapes could also be provided.

The web member 30 preferably includes a plurality of inflation openings 34, such as illustrated in FIG. 2. These openings permit fluid flow through web member, thus allowing fluid communication to both sides of web member.

Figure 5:
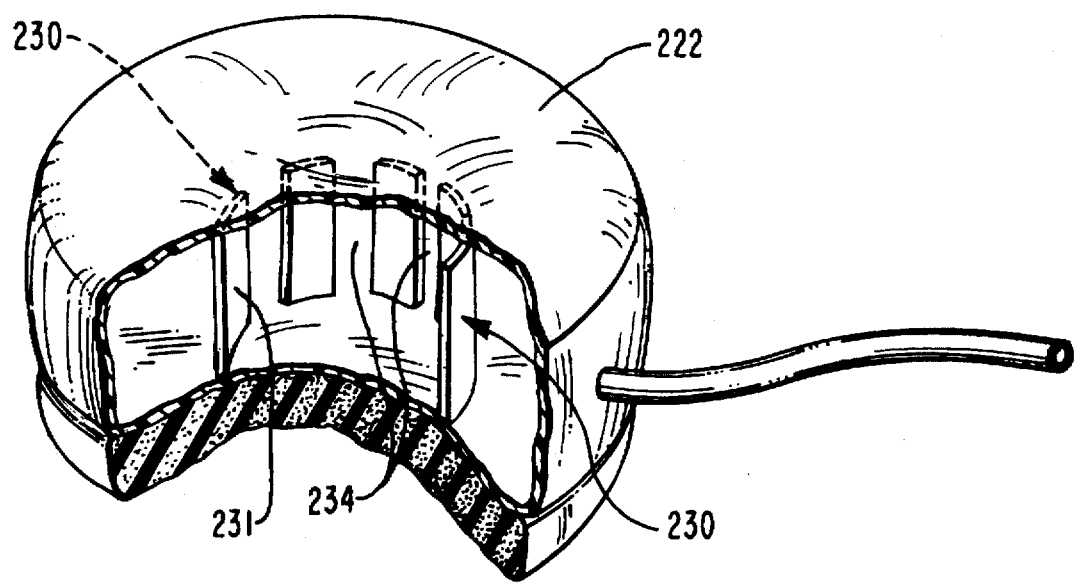
FIG. 5 is a cross sectional view of yet another alternate embodiment of the apparatus of the present invention.

Alternatively, as illustrated in FIG. 5, web member 230 comprises individual web portions 231 such that inflation openings are not necessitated. Instead, the open areas 234 between the individual web portions allow fluid communication throughout the interior of inflatable chamber 222.

The posterior surface 32 offers a base which facilitates positioning and retention of the apparatus on the chest wall. The posterior surface generally responds to the constraints of the web mechanism in substantially the same manner as the anterior surface, and is either substantially flat as illustrated in FIG. 2, or substantially concave as illustrated in FIG. 3. However, it should be appreciated that the posterior surface is not limited to the configuration exhibited by the anterior surface. FIG. 4 illustrates an embodiment of the present invention wherein anterior surface 128 of inflatable chamber 122 tapers according to the constraints of web member 130, while posterior surface 132 remains substantially flat.

In a preferred embodiment of the present invention illustrated in FIG. 2, the flat posterior surface 32 further comprises an insulation pad 26 which serves to insulate the phrenic nerves from the frigid bathes commonly employed in cardiac surgical procedures. The insulation pad 26 also protects the nerves from any compressive forces exerted by the weight of present invention in concert with the weight of the heart, and the surgery being performed thereon.

The insulation pad 26 is preferably of a thickness of 1-5 mm, although other thicknesses are within the scope of the present invention. It is further a feature of the present invention that insulation pad 26 comprises open or closed cell foam which serves to insulate by trapping air in bubbles in the foam. Suitable materials for the foam include, but are not limited to, neoprene, silicone, urethane, and combinations thereof.

Furthermore, it is a feature of the present invention that the insulation pad 26 is soft and deformable to fit the gradations of the posterior chest wall. Additionally, the insulation pad preferably conforms to the shape of the posterior surface. FIG. 3, for example, illustrates insulation pad 26 conforming to the concave shape of the concave posterior surface 32. In addition, FIG. 4 illustrates insulation pad 126 conforming to the flat shape of posterior surface 132, while anterior surface 128 remains tapered.

Upon inflation, the inflatable chamber, is sized to accommodate the bulk of the heart muscle. A preferred diameter for an adult human patient is approximately 2 to 5 inches across. It should be understood, however, that larger or smaller diameters would be within the scope of the present, as per the needs of the surgeon.

In addition, the inflatable chamber provides approximately 0 to 6 centimeters of lift from the chest wall in an embodiment preferred for an adult human. It should also be understood, however, that the amount of lift could be increased or decreased according to the needs of the surgeon by over inflating or under inflating the inflatable chamber. It would also be within the scope of the present invention to provide various sizes of inflatable chambers to accommodate the differing dimensions of various patients.

In order to inflate and deflate inflation chamber, the present invention comprises access port 23. As illustrated in FIG. 2, the access port 23 preferably opens into the inflation chamber just superior to the posterior surface 32 of inflation chamber. It should be understood, however, that the access port could open into the inflation chamber at alternate locations.

In a preferred embodiment of the present invention illustrated in FIG. 2, inflation tubing 24 is inserted through access port 23 such that inflation tubing is in fluid communication with the inside of inflation chamber. Similarly, FIG. 4 illustrates inflation tubing 124 which enters inflatable chamber 122 through access port 123. In one embodiment of the present invention, inflation tubing is bonded to inflation chamber. In an alternate embodiment, the inflation tubing is removable.

In a preferred embodiment illustrated in FIGS. 1 and 2, a valve mechanism 36 is connected to inflation tubing 24. The valve mechanism offers selective inflation and deflation as per the requirements of the surgeon. Alternatively, other selective opening mechanisms would be within the scope of the present invention. For example, "T" or "Y" valves, or luer locks would also allow selective inflation and deflation of the inflation chamber.

It is a feature of the present invention that inflation chamber can be inflated with air. Air is particularly useful as it additionally serves as an insulator to prevent cold shock to the phrenic nerves. Alternatively, the inflation chamber may be inflated with cold sterile saline solution or any other such medium the surgeon selects.

The present invention also relates to a method for use of the inflatable heart elevation apparatus. For example, in a procedure wherein a medium sternotomy has been performed, the apparatus of the present invention is preferably inserted in a deflated state. The apparatus is positioned beneath the heart along the chest wall, such that the heart balances stably thereon. The apparatus is then selectively inflated, which elevates the heart and improves the surgeon's access thereto. After completion of the cardiac surgical procedure, the apparatus is deflated by applying suction in the form a syringe or a vacuum, and then removed from the patient.

Alternatively, in a procedure wherein a thoracotomy has been performed, the apparatus is preferably inserted through the open rib incision. In a deflated state, the apparatus is preferably folded or rolled into a tube and slipped through the thoracotomy and positioned under heart. The apparatus is then inflated, which positions the heart close to the thoracotomy. After completion of the cardiac procedure, the device is deflated and carefully removed.

It should also be understood that the aforementioned methods are in no way limiting to the scope of the present invention. Alternate methods for using the inflatable heart elevator would also be envisioned by the present invention. In addition, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for improved positioning of cardiac tissue during cardiac surgical procedures, comprising:
   a. an inflatable chamber, said inflatable chamber further comprising:
      i) an interior space;
      ii) an anterior surface; and
      iii) a posterior surface;
   b. an insulation pad affixed to said posterior surface of said inflatable chamber; and
   c. an access port communicating with said interior space of inflatable chamber through which said inflatable chamber may be inflated and deflated.

2. An apparatus as recited in claim 1, wherein said inflatable chamber is substantially cylindrical.

3. An apparatus as recited in claim 1, wherein said inflatable chamber is comprised of a material having a durometer of about 20 shore A to about 90 shore D.

4. An apparatus as recited in claim 3, wherein said material is a urethane composition.

5. An apparatus as recited in claim 1, wherein said anterior surface and said posterior surface are substantially flat.

6. An apparatus as recited in claim 1, wherein said anterior surface and said posterior surface are substantially concave.

7. An apparatus as recited in claim 1, wherein said inflatable chamber further comprises a web member, said web member constraining said anterior surface and said posterior surface of said inflatable chamber.

8. An apparatus as recited in claim 7, wherein said web member further includes a plurality of inflation openings, said inflation openings allowing fluid communication throughout said interior space of said inflatable chamber.

9. An apparatus as recited in claim 1, wherein said insulation pad substantially conforms to the shape of said posterior surface of said inflatable chamber.

10. An apparatus as recited in claim 1, wherein said insulation pad comprises a sufficient thickness so that it will provide insulation for the phrenic nerves during use with cold, sterile fluids in the chest cavity.

11. An apparatus as recited in claim 10, wherein said thickness is from about 1 to about 5 millimeters.

12. An apparatus as recited in claim 1, wherein said access port further comprises inflation tubing in fluid communication with said interior space of inflation chamber.

13. An apparatus as recited in claim 12, further comprising a valve mechanism affixed to said inflation tubing, said valve mechanism allowing selective inflation and deflation of said inflatable chamber.

14. An apparatus for improving positioning of cardiac tissue during cardiac surgical procedures, comprising:
   a. a substantially cylindrical inflatable chamber, said inflatable chamber further comprising:
      i) an interior space;
      ii) an anterior surface; and
      iii) a posterior surface;

b. an insulation pad affixed to said posterior surface of said inflation chamber, said inflation pad further comprising a sufficient thickness so that will provide insulation for the phrenic nerves during use with cold, sterile fluids in the chest cavity;

c. an access port communicating with said interior space of said inflatable chamber through which said inflatable chamber may be inflated and deflated, said access port further comprising inflation tubing in fluid communication with said interior space of said inflatable chamber; and d. a web member attached to said inflatable chamber, said web member constraining said anterior surface and said posterior surface of said inflatable chamber, said web member further allowing fluid communication throughout said interior space of said inflatable chamber.

15. An apparatus as recited in claim 14, wherein said anterior surface and said posterior surface are substantially flat.

16. An apparatus as recited in claim 14, wherein said anterior surface and said posterior surface are substantially concave.

17. A method for improved positioning of cardiac tissue during cardiac surgical procedures while avoiding damage to the phrenic nerves, comprising the steps of:

a. obtaining an apparatus for improving access to cardiac tissue comprising:
   1) an inflatable chamber, said inflatable chamber further comprising an interior space, an anterior surface and a posterior surface;
   2) an insulation pad affixed to said posterior surface for protecting the phrenic nerves; and
   3) an access port for inflating said inflatable chamber;

b. introducing said apparatus through an incision in a chest of a subject;

c. positioning said apparatus underneath a heart in said subject; and d. inflating said apparatus so as to position the heart to improve a surgeon's access thereto.

18. A method according to claim 17, wherein said apparatus is inflated with air.

19. A method according to claim 17, wherein said apparatus is inflated with cold saline solution.

20. A method according to claim 17, wherein said apparatus is removed and inserted in a deflated state.

* * * * *

UNITED STATES PATENT AND TRADEMARK OFFICE
CERTIFICATE OF CORRECTION

PATENT NO. : 5,735,791

DATED : Apr. 7, 1998

INVENTOR(S) : John C. Alexander, Jr.; Carl A. Swindle

It is certified that error appears in the above-identified patent and that said Letters Patent is hereby corrected as shown below:

Col. 2, line 46, after "form" insert --of--

Col. 5, line 62, after "under" insert --the--

Col. 7, line 2, after "said" change "inflation" (second occurrence) to --insulation--

Col. 7, line 3, after "that" insert --it--

Signed and Sealed this

Sixteenth Day of February, 1999

Attest:

*Attesting Officer*

*Acting Commissioner of Patents and Trademarks*